United States Patent
Fabricant

[19]

[11] Patent Number: 5,842,294
[45] Date of Patent: Dec. 1, 1998

[54] GOLF ORTHOTIC

[75] Inventor: B. Robert Fabricant, Boca Raton, Fla.

[73] Assignee: Dr. Fabricant's Foot Health Products Inc., Hauppauge, N.Y.

[21] Appl. No.: 608,192

[22] Filed: Feb. 28, 1996

[51] Int. Cl.⁶ .................. A61F 5/14; A43B 7/14
[52] U.S. Cl. .............. 36/127; 36/173; 36/154; 36/144
[58] Field of Search .................. 36/43, 44, 142, 36/143, 144, 145, 154, 166, 173

[56] References Cited

U.S. PATENT DOCUMENTS

| Re. 33,648 | 7/1991 | Brown | 36/154 |
|---|---|---|---|
| 865,836 | 9/1907 | Wedekind | 36/154 |
| 2,348,300 | 5/1944 | Klaus | 36/154 |
| 2,821,032 | 1/1958 | Helfet | 36/154 |
| 3,068,872 | 12/1962 | Brody | 36/154 |
| 3,545,447 | 12/1970 | Silverman | 36/142 |
| 4,694,589 | 9/1987 | Sullivan | 36/43 |
| 4,702,255 | 10/1987 | Schenkel | 36/154 |
| 4,759,357 | 7/1988 | Allart et al. | 36/143 |
| 4,791,736 | 12/1988 | Phillips | 36/43 |

FOREIGN PATENT DOCUMENTS

| 2016000 | 10/1971 | Germany | 36/145 |
|---|---|---|---|

OTHER PUBLICATIONS

Steven J. Levitz et al. "Biomechanical Foot Therapy" pp.729–731 (no date available).

Primary Examiner—Paul T. Sewell
Assistant Examiner—Anthony Stashick
Attorney, Agent, or Firm—Hoffmann & Baron, LLP

[57] ABSTRACT

A golf orthotic for stabilizing a foot of a patient against both supination and pronation includes a main body portion configured to conform to a substantial portion of the plantar aspect of the patient's fool, including the heel and arch, and generally forward to the metatarsal heads. The main portion is provided with medial and lateral flanges terminating respectively beneath the medial malleolus and lateral malleolus. The device also includes a heel stabilization bar with a substantially flat lower surface and an upper surface which is contoured to match the lower surface of the main portion in the heel region, and which is secured thereto. The heel stabilization bar is shaped for easy insertion into the patient's shoe. The flanges are shaped to conform to the patient's foot, and preferably slope up fairly steeply from the main body portion. A preferred method of manufacturing the device, as well as methods for using it to treat chronic weak ankle syndrome and to prevent ligamentous damage, are also disclosed.

1 Claim, 5 Drawing Sheets

GOLF ORTHOTIC

BACKGROUND OF THE INVENTION

1. Field of the Invention

The present invention relates to podiatric devices, and more particularly relates to a golf orthotic.

2. Description of the Prior Art

Orthotics are well-known podiatric devices. They are designed to support and stabilize the foot during various sports activities, or as an aid to treat or even prevent certain trauma, such as ankle strain. Prior art orthotic devices generally include a "stopper," known as a medial flange, on the inside of the orthotic, in order to prevent over-pronation of the foot (i.e., excessive rolling of the foot onto its medial aspect, or inside surface). During a typical golf swing of a right-handed player, the player's left foot pronates and right foot supinates (i.e., rolls onto its lateral aspect, or outside surface). The opposite happens during the forward swing. While prior art devices may be effective in preventing over-pronation, they do not aid in prevention of over-supination. One prior art device, the so-called Whitman plate, provides small flanges for both the lateral and medial aspects. These flanges are too small and too gradually sloped to provide adequate stabilization. Further, no prior art orthotic, including the Whitman plate, provides any protection against calcaneal deviation (heel instability). A further disadvantage of the Whitman plate is that it is constructed from substantially rigid steel, and so cannot provide gentle, resilient support.

In view of the deficiencies of prior art orthotic devices, there is a need for an orthotic device which affords protection against both over-pronation and over-supination. Furthermore, there is also a need for an orthotic device which reduces or eliminates calcaneal deviation, and which provides gentle, resilient support.

OBJECTS AND SUMMARY OF THE INVENTION

It is an object of the present invention to provide an orthotic which protects against both over-pronation and over-supination.

It is another object of the present invention to provide an orthotic which affords protection against calcaneal deviation.

It is yet another object of the present invention to provide an orthotic suitable for stabilizing the feet of a golfer.

It is a further object of the present invention to provide a method of treating chronic weak ankles by means of an orthotic device in accordance with the invention.

It is yet a further object of the present invention to provide a method of preventing ligamentous damage by means of an orthotic device in accordance with the invention.

It is an additional object of the present invention to provide an orthotic which affords gentle, resilient support.

In accordance with one form of the present invention, an orthotic device for stabilizing a foot of a patient against both supination and pronation includes a main body portion having upper and lower surfaces, a front edge, a medial region, a lateral region, and a heel region. The main body portion is configured to conform to at least a substantial portion of the plantar aspect of the patient's foot, including the heel and arch. The main body generally extends as far forward as the metatarsal heads, where the front edge is located. The orthotic device also includes a medial flange which is secured to the medial region of the main body portion and is configured to conform to the medial aspect of the patient's foot. The medial flange extends upwardly about the arch of the patient's foot and terminates beneath the medial malleolus.

A lateral flange is also included in the orthotic device. The lateral flange is secured to the lateral region of the main body portion and is configured to conform to the lateral aspect of the patient's foot. The lateral flange extends upwardly about the lateral aspect of the foot and terminates beneath the lateral malleolus. The medial and lateral flanges, as well as the main body portion, are preferably made of a resilient material. The orthotic device further includes a heel stabilization bar having a substantially flat lower surface, an upper surface contoured to match the lower surface of the main body portion in the heel region, and a perimetric edge shaped for easy insertion into the patient's shoe. The upper surface of the stabilization bar is secured to the lower surface of the main body portion in the heel region.

In a method, according to the present invention, of treating a patient for chronic weak ankle syndrome associated with sprained lateral collateral ligaments, an orthotic device in accordance with the present invention is provided and is placed within a shoe of the patient. The patient then wears the shoe with the emplaced orthotic device, thus supporting the lateral collateral ligaments and preventing further spraining or stretching.

In a method, according to the present invention, of preventing ligamentous damage in a patient, an orthotic device in accordance with the present invention is provided and is placed within a shoe of the patient. The patient then wears the emplaced orthotic device, thus supporting the lateral and medial collateral ligaments and preventing damage to the ligaments.

In a method, according to the present invention, of manufacturing an orthotic device to conform to a foot of a patient, a negative cast is made of the patient's foot and is then used to produce a substantially rigid positive cast of the foot by pouring a hardenable material into the negative cast. A relatively thin sheet of engineering polymer is then formed about the positive cast to obtain a portion of an orthotic in accordance with the present invention, including the main portion and the medial and lateral flanges. Finally, a heel stabilizer bar as described above is secured to the lower surface of the main body portion in the heel region.

These and other objects, features and advantages of the present invention will become apparent from the following detailed description of illustrative embodiments thereof, which is to be read in connection with the accompanying drawings.

DETAILED DESCRIPTION OF THE PREFERRED EMBODIMENT

Figure 1:
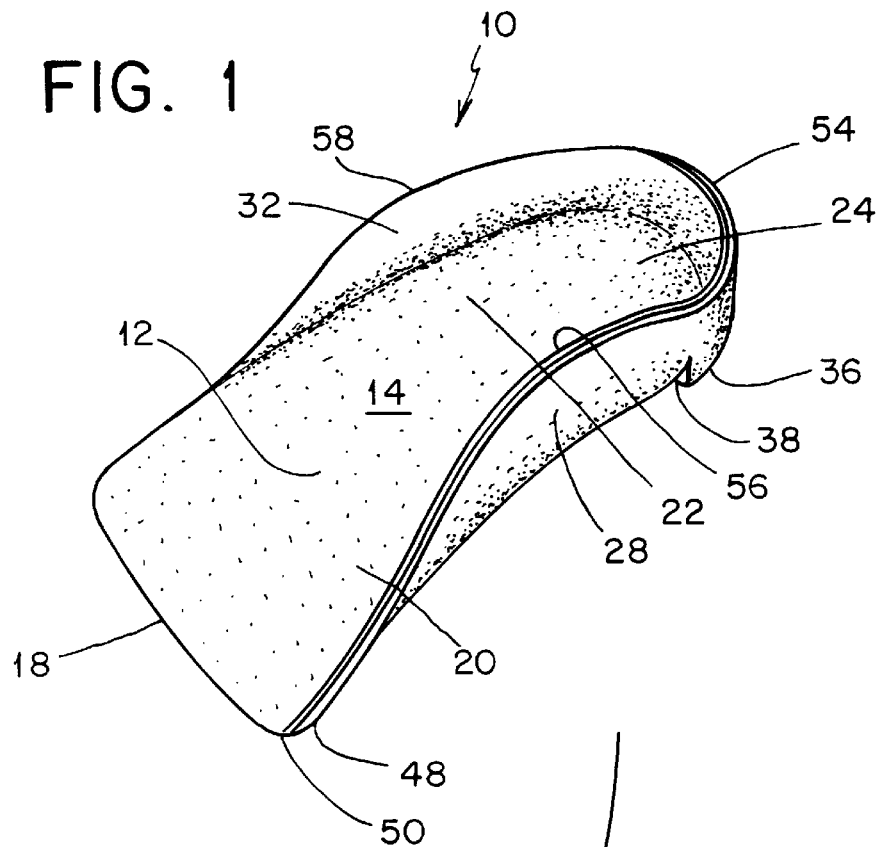
FIG. 1 is a perspective view of an orthotic device in accordance with the invention.
Figure 2:
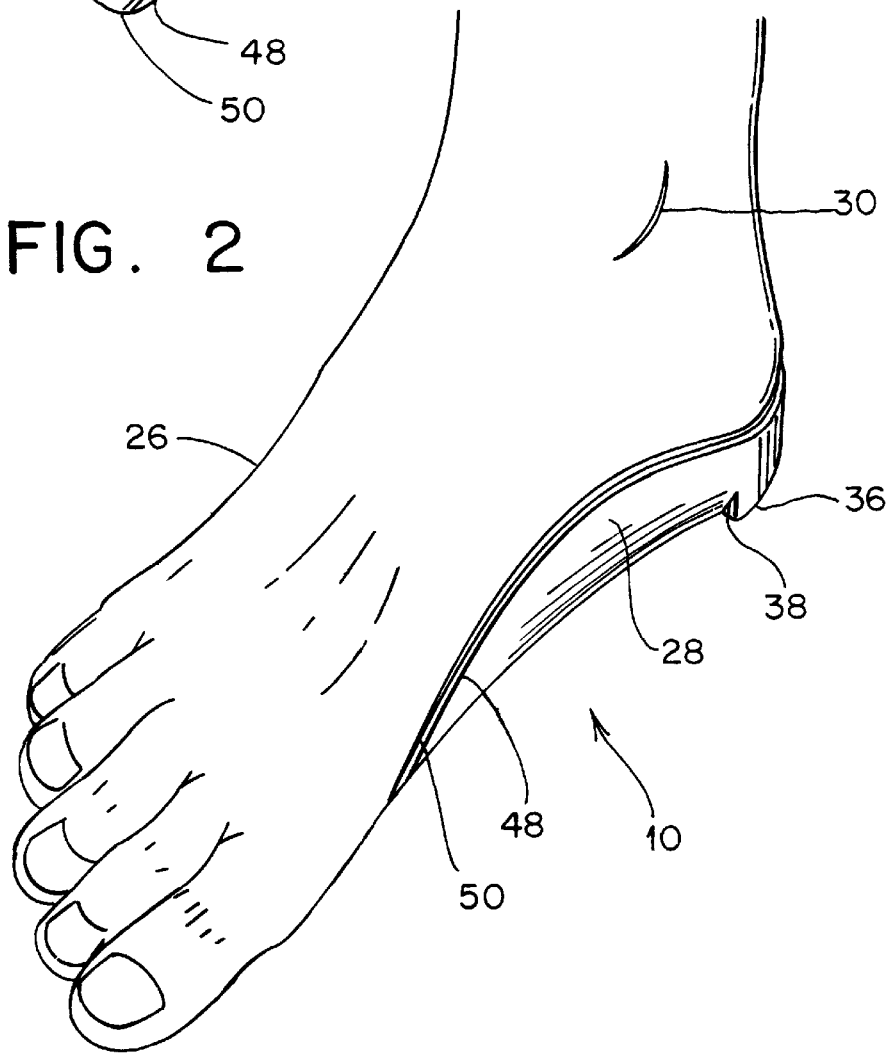
FIG. 2 is a perspective view of the medial aspect of the orthotic device of FIG. 1 located about the right foot of a patient.
Figure 3:
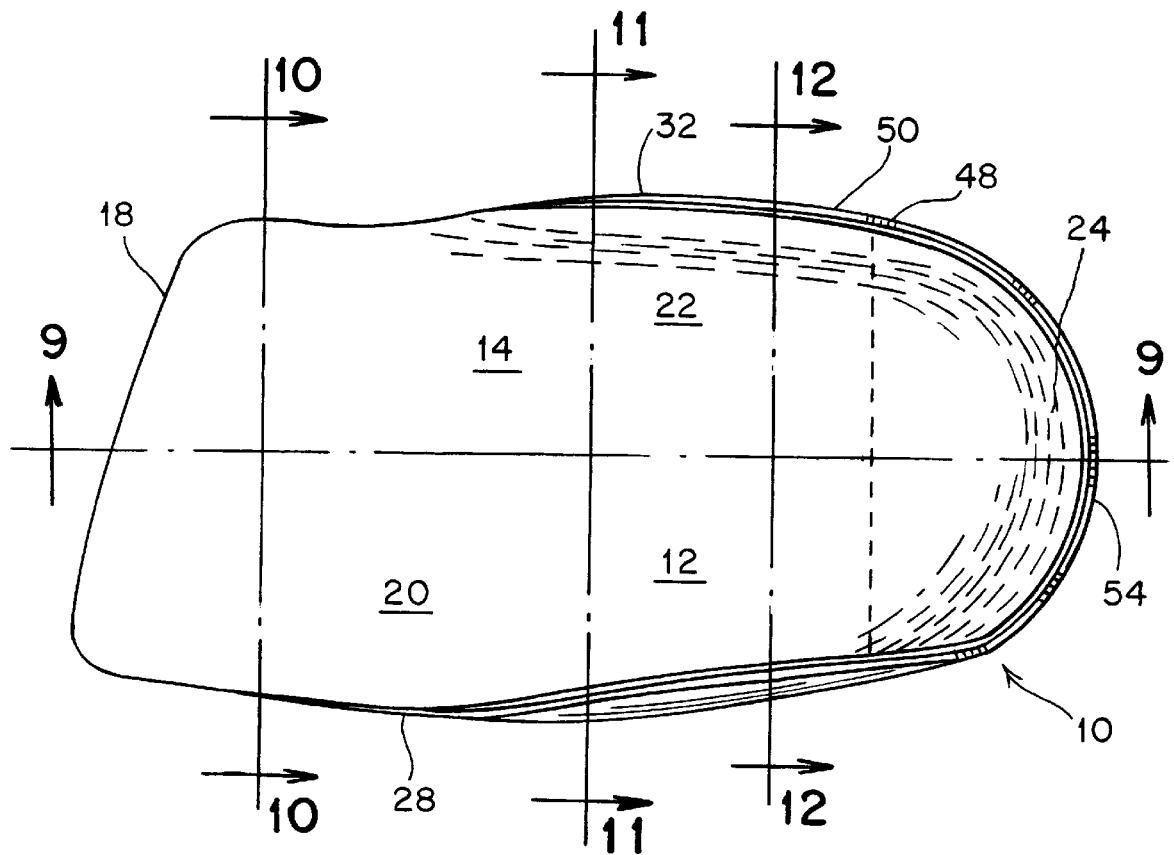
FIG. 3 is a top plan view of the orthotic device of FIG. 1.
Figure 5:
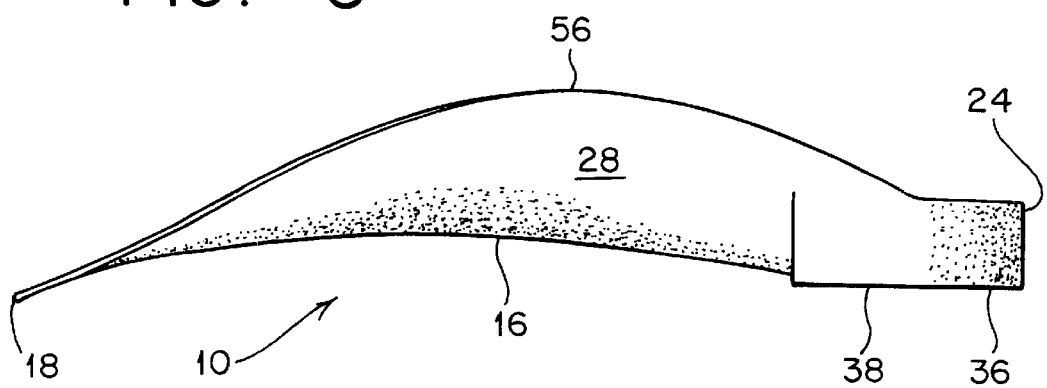
FIG. 5 is an elevational view showing the medial aspect of the orthotic device of FIG. 1.

Referring first to FIG. 1, orthotic device 10 includes a main body portion 12 having upper surface 14 and lower surface 16 (not visible in FIG. 1). The main body portion 12 also has a front edge 18, a medial region 20 (as best seen in FIG. 3), a lateral region 22, and a heel region 24. The main body portion 12 is configured to conform to at least a substantial portion of the plantar aspect of the patient's foot 26 (as shown in FIG. 2), including the heel and arch of the foot, and generally forward to the metatarsal heads.

Still referring to FIG. 1, device 10 also includes a medial flange 28 secured to medial region 20 of main body portion 12. Medial flange 28 is configured to conform to the medial aspect of the patient's foot 26, as best seen in FIG. 2. The medial flange extends upwardly about the arch of foot 26, and terminates beneath the medial malleolus 30 of foot 26.

Figure 13:
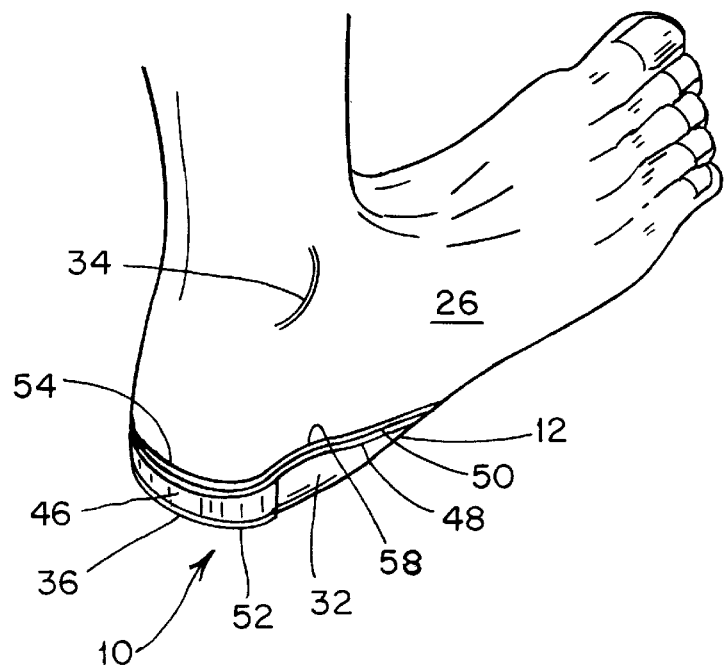
FIG. 13 is a perspective view of the lateral aspect of the orthotic device of FIG. 1 located about the right foot of a patient.

Referring again to FIG. 1, device 10 also includes a lateral flange 32 secured to lateral region 22 of main body portion 12. Lateral flange 32 is configured to conform to the lateral aspect of the patient's foot 26, as best seen in FIG. 13. The lateral flange extends upward about the lateral aspect of the foot 26, and terminates beneath the lateral malleolus 34 of foot 26.

Figure 4:
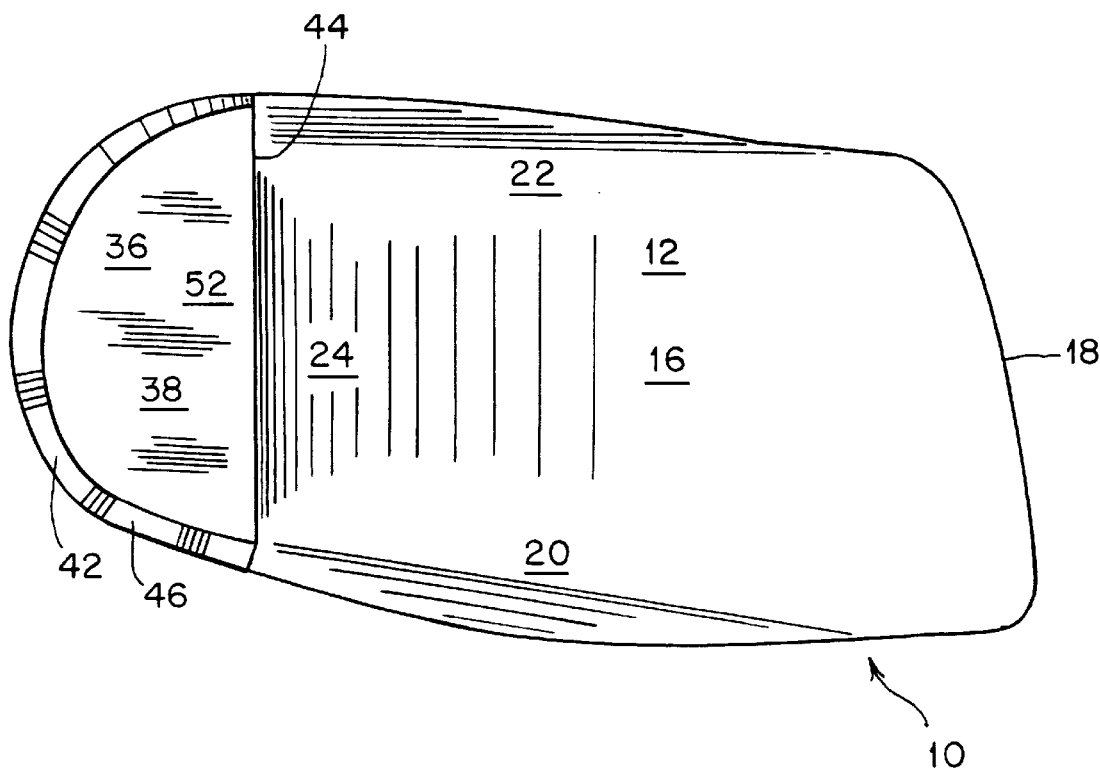
FIG. 4 is a bottom plan view of the orthotic device of FIG. 1.

Referring now to FIGS. 1, 2, 4–7 and 9, orthotic device 10 also includes a heel stabilization bar 36 having a substantially flat lower surface 38 and an upper surface 40 contoured to match the lower surface 16 of main body portion 12 (and adjacent portions of the flanges) in heel region 24. Bar 36 also has a perimetric edge 42 (as best seen in FIG. 4) shaped for easy insertion into a shoe of the patient. Edge 42 preferably includes straight front edge 44 and rear curved surface 46 which conforms generally to the contours of heel region 24. Upper surface 40 of bar 36 is secured to lower surface 16 of main body portion 12 in heel region 24.

Preferably, main body portion 12, medial flange 28 and lateral flange 32 are formed as a unitary structure made from a flexible engineering polymer exhibiting intrinsic memory and recall, a room-temperature flexural modulus of about 350,000 psi and a tensile strength of about 7400 psi. A preferred polymeric material is that which is available from Ever-Flex Laboratories of Lincoln Park, Mich. Preferably, the unitary structure is a curved sheet 48 having a thickness of about 1 mm. Sheet 48 is preferably covered with thin vinyl padding 50 on upper surface 14 of main body portion 12, extending onto medial and lateral flanges 28 and 32. Use of the preferred material results in a device capable of gentle, resilient support. As compared to a substantially rigid steel device such as the Whitman plate, the resilience of the present device permits greater deflection of the device in response to foot motion, with more gentle restorative forces to return the foot to its preferred position.

Heel stabilization bar 36 is preferably constructed of a rubber-based ethylene-vinyl acetate (EVA) material exhibiting a Shore A durometer hardness between 60 and 70. It may also include a bottom layer 52 of vinyl padding. The vinyl padding 50, 52 may be of simulated kidskin for purposes of softness, comfort and durability. A preferred method of manufacturing device 10 will be set forth below.

It is preferable that medial and lateral flanges 28 and 32 extend towards and meet each other at heel region 24 of main body portion 12, thereby forming a heel counter lip 54, which provides further support for the heel of the patient's foot 26.

Figure 8:
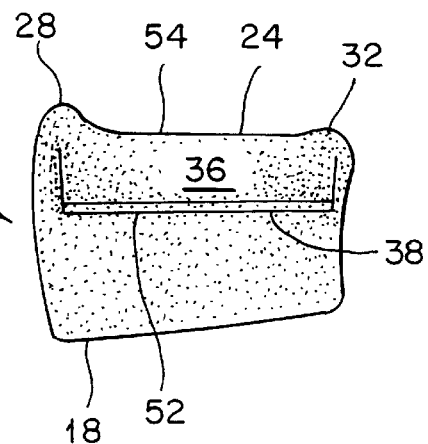
FIG. 8 is an elevational view showing the heel of the orthotic device of FIG. 1.
Figure 9:
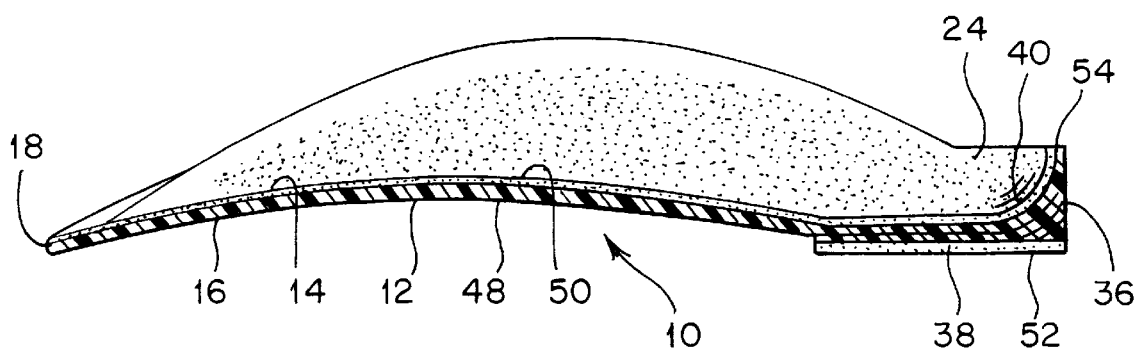
FIG. 9 is a longitudinal section taken along line 9—9 of FIG. 3.
Figure 10:
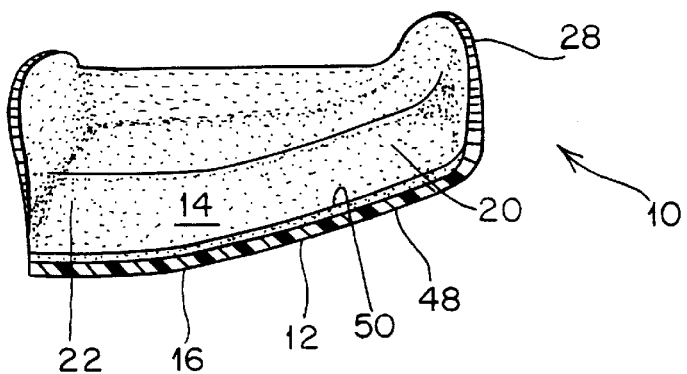
FIG. 10 is a transverse section taken along line 10—10 of FIG. 3.
Figure 11:
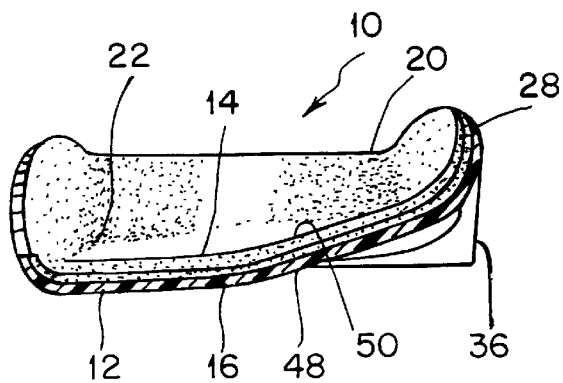
FIG. 11 is a transverse section taken along line 11—11 of FIG. 3.
Figure 12:
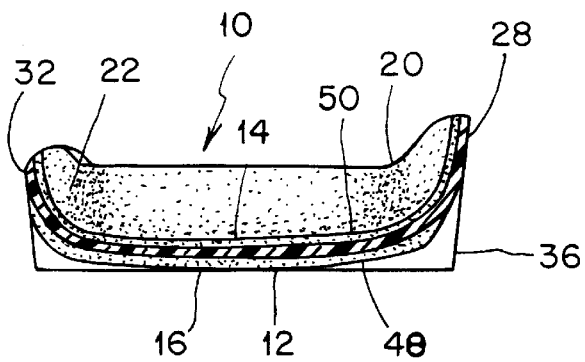
FIG. 12 is a transverse section taken along line 12—12 of FIG. 3.

Referring briefly to FIG. 8, which is an elevational view of the orthotic device 10 from the heel, looking parallel to lower surface 38 of heel stabilization bar 36, it can be seen that front edge 18 actually extends somewhat below surface 38 when there is no weight on device 10.

Figure 6:
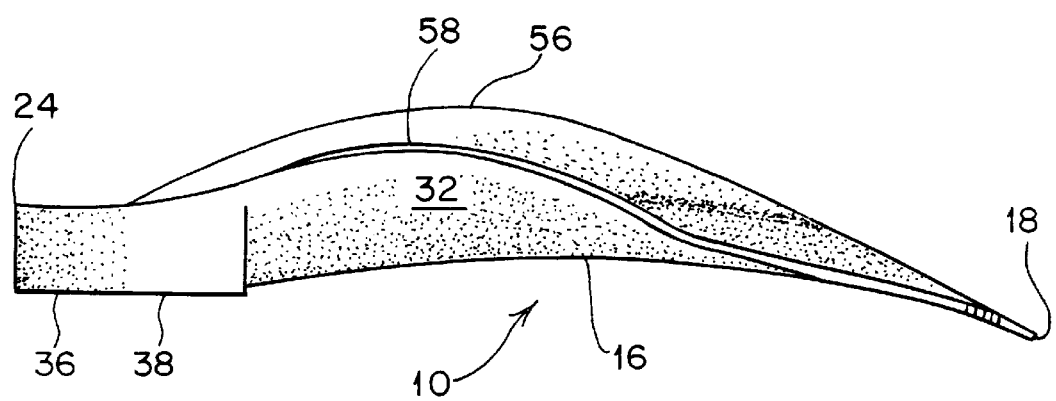
FIG. 6 is an elevational view showing the lateral aspect of the orthotic device of FIG. 1.
Figure 7:
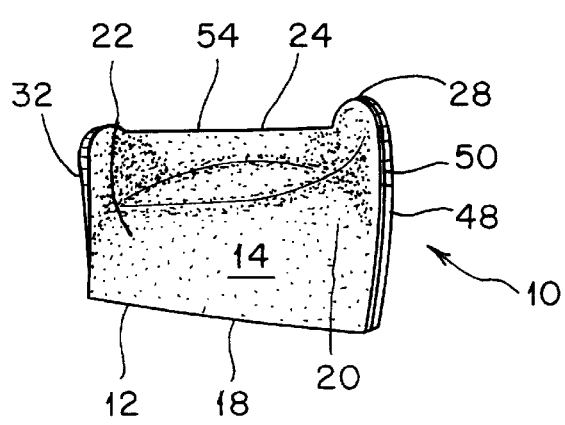
FIG. 7 is an elevational view showing the front of the orthotic device of FIG. 1.

It has been found that medial and lateral flanges 28 and 32 provide the best support, and have the greatest inhibitive effect on pronation and supination, when they slope upward relatively steeply from main body portion 12. Flanges 28 and 32 preferably each exhibit a point of maximum height (56 and 58, respectively). As best seen in FIG. 6, point 58 of lateral flange 32 is preferably closer to heel region 24 than is point 56 of medial flange 28, in order to conform to the normal morphology of the foot. Point 56 of medial flange 28 will generally be higher than point 58 of lateral flange 32 in absolute terms, that is, when measured relative to a flat surface on which the orthotic device 10 has been placed. However, due in part to the arch-conforming slope of main body portion 12, which increases in height from the lateral region to the medial region, point 58 of lateral flange 32 will generally be higher than point 56 of medial flange 28 in relative terms, that is, measured relative to the adjacent regions of main body portion 12.

In use, device 10 has been found to prevent overpronation and over-supination both in terms of rolling and of translational motions of the foot. Further, the heel stabilization bar 36, also known as a "post," prevents both inversion and rolling of heel. Device 10 will cause a golfer to place his weight on the forefeet. The combined protection against both over-pronation and over-supination, coupled with stabilization of the heel and weight transfer, provides a balanced hitting platform of great benefit to the golfer.

It is to be understood that, although the present invention is well-suited to use in the game of golf, it may be beneficially employed in any sport or activity wherein the player or participant is generally stationary. It is believed that the present invention is less well suited to sports requiring rapid cutting and swerving motions (e.g., those of a tennis player or a football running back). However, the present invention has been found to be beneficial for wear during all activities when treating chronic weak ankle syndrome, or when worn prophylactically against ligamentous damage.

In chronic weak ankle syndrome, ligaments which have been stretched do not heal completely, and remain somewhat lengthened, causing instability of the ankle. Most frequently, it is the ligaments on the outside of the ankle (the lateral collateral ligaments) which are damaged. The typical prior-art orthotic used for treatment employs only a medial flange which raises the medial aspect of the foot and lowers the lateral aspect, exacerbating rather than helping the overstretched condition of the outer ligaments.

In a method, according to the present invention, of treating a patient for chronic weak ankle syndrome associated with sprained lateral collateral ligaments, an orthotic device in accordance with the present invention is provided and is placed within the patient's shoe. (It is to be understood that the orthotic devices will usually be employed in pairs). The patient then wears the shoe with the emplaced orthotic device, in order to support the lateral collateral ligaments and prevent any further spraining or stretching thereof.

As previously noted, the present invention has utility in preventing ligamentous damage. In a method, according to the present invention, of preventing ligamentous damage in a patient, an orthotic device in accordance with the present invention is provided and is placed within the patient's shoe. The shoe is then worn with the emplaced orthotic device, resulting in support and stabilization of the foot and heel, with concomitant reduction or elimination of the threat of ligamentous damage.

A preferred method of manufacturing an orthotic device in accordance with the present invention includes the steps of making a negative cast of the foot of the patient, for example, in a foam material, followed by making a substantially rigid positive cast of the foot by pouring a hardenable material, such as plaster, into the negative cast. A relatively thin sheet of engineering polymer is then formed about the positive cast to obtain a curved unitary sheet 48 including main body portion 12, medial flange 28 and lateral flange 32. Unitary sheet 48 may also include heel counter lip 54. A thickness of about 1 mm is preferred. Sheet 48 is trimmed so that it extends no further forward than the metatarsal heads, and so that the medial and lateral flanges 28 and 32 extend no further upward than the medial malleolus 30 and lateral malleolus 34, respectively. Heel counter lip 54, if present, may also be trimmed to a convenient height, if desired. Vinyl padding 50 may then be secured to sheet 48 via adhesive or other means, and trimmed to fit.

A suitable heel stabilization bar 36 is then sculpted of a material such as the above-mentioned rubber-based EVA and is secured to lower surface 16 of main portion 12 in heel region 24 by, for example, bonding with a suitable adhesive. It is to be understood that the heel stabilization bar 36 is preferably sculpted to transition smoothly into the heel region 24 as well as adjacent portions of the medial and lateral flanges 28, 32 and heel counter lip 54 (if present). The bottom layer 52, of vinyl padding or similar material, may then be secured to the heel stabilization bar 36, if desired, via adhesive or other suitable means.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A golf orthotic for stabilizing a foot of a patient against both supination and pronation, said orthotic comprising:

a main body portion having upper and lower surfaces, a front edge, a medial region, a lateral region, and a heel region, said main body portion being configured to substantially conform to the plantar aspect of the patient's foot, including the heel and arch thereof, and generally forward to the metatarsal heads of the foot;

medial flange means for inhibiting over-pronation of said foot, said medial flange means being secured to said medial region of said main body portion and configured to conform to the medial aspect of the patient's foot, said medial flange means extending upwardly about the arch of the foot and terminating beneath the medial malleolus of the foot;

lateral flange means for inhibiting over-supination of said foot, said lateral flange means being secured to said lateral region of said main body portion and configured to conform to the lateral aspect of the patient's foot, said lateral flange means extending upwardly about the lateral aspect of the foot and terminating beneath the lateral malleolus of the foot; and a heel stabilization bar having a substantially flat lower surface, an upper surface contoured to match said lower surface of said main body portion in said heel region, and a perimetric edge shaped for easy insertion into a shoe of the patient, said upper surface of said bar being secured to said lower surface of said main body portion in said heel region;

wherein:

said main body portion, said medial flange means, and said lateral flange means are formed from a material which exhibits a room-temperature flexural modulus of approximately 350,000 psi; and said main body portion, said medial flange means, and said lateral flange means are formed as a unitary structure with a thickness of about 1 mm.

* * * * *